United States Patent [19]

Johnson et al.

[11] 4,020,830
[45] May 3, 1977

[54] SELECTIVE CHEMICAL SENSITIVE FET TRANSDUCERS

[75] Inventors: Curtis C. Johnson, Sandy; Stanley D. Moss, Kaysville; Jiri A. Janata, Salt Lake City, all of Utah

[73] Assignee: The University of Utah, Salt Lake City, Utah

[22] Filed: Mar. 12, 1975

[21] Appl. No.: 557,545

[52] U.S. Cl. .................. 128/2 E; 195/103.5 R; 195/127; 204/195 M; 204/195 P; 204/195 S; 204/195 B; 324/29; 357/25
[51] Int. Cl.² ................ A61B 5/05; G01N 27/46; G01N 31/14
[58] Field of Search ............... 128/2E, 2 G, 2.1 E; 204/195, 1; 195/103.5, 127; 324/71 SN, 29, 30; 357/25

[56] References Cited

UNITED STATES PATENTS

| 3,049,118 | 8/1962 | Arthur et al. | 128/2 E |
|---|---|---|---|
| 3,294,988 | 12/1966 | Packard | 310/8 |
| 3,649,505 | 3/1972 | Strickler et al. | 204/195 |
| 3,776,819 | 12/1973 | Williams | 204/1 E |
| 3,787,309 | 1/1974 | Neti et al. | 204/195 M |
| 3,831,432 | 8/1974 | Cox | 73/23 |
| 3,896,008 | 7/1975 | Keyes | 204/1 E |
| 3,932,233 | 1/1976 | Ruzicka et al. | 204/195 M |

OTHER PUBLICATIONS

P. Bergveld, IEEE Trans. on Bio–Med. Eng., pp. 70–71, Jan. 1970.
Tadayuki Matsuo et al., IEEE Trans. on Bio-Med. Eng., pp. 485–487, Nov. 1974.
Piet Bergveld, IEEE Trans. on Bio–Med Eng., vol. BME–19, No. 5, pp. 342–351, Sept. 1972.
Gary R. Rechnitz, C & EN, pp. 29–35, Jan. 27, 1975.

*Primary Examiner*—G. L. Kaplan
*Attorney, Agent, or Firm*—Criddle, Thorpe & Western

[57] ABSTRACT

A chemical sensitive field-effect transistor transducer capable of selectively detecting and measuring chemical properties of substances to which the transducer is exposed. The transducer includes a semiconductor substrate material having a certain doping polarity, a pair of spaced apart diffusion regions located at the surface of the substrate material and having a doping polarity opposite that of the substrate material, electrical insulator material overlying the diffusion regions and the surface of the substrate material lying between the diffusion regions, and a chemical selective system overlying the insulator material. The chemical selective system is adapted to interact with certain substances and thereby modulate an electric field produced in the substrate material between the diffusion regions. This modulation is dependent upon the chemical properties of the substances and provides a measure of those chemical properties. The chemical selective system may include various structures for measuring ion activity, immunochemical concentrations, reducible gas concentrations and the concentrations of enzymes and substrates.

27 Claims, 11 Drawing Figures

SELECTIVE CHEMICAL SENSITIVE FET TRANSDUCERS

BACKGROUND OF THE INVENTION

This invention relates to a field effect transistor transducer adapted for detection and measurement of various chemical properties such as ion activity.

There has been a continuing search for improved methods of in vivo detection, measurement and monitoring of chemical properties. ("Chemical properties", as used herein, shall be understood to include ion activity and concentration, presence and concentration of enzymes, substrates, antibodies, antigens, hormones and reducible gases and the presence, concentration and activity of any of a variety of chemical and biochemical substances.) For example, in patients with arrhythmias, cardiogenic shock, and myocardial infarctions, various ion concentrations in the body of the patient may shift dramatically in the course of treatment of the patient and measurement and monitoring of such shifts can provide an important indication as to the well being of the patient. Change of ion concentration in the body of a patient is also common during open heart or major vascular surgery, during pharmacological therapy, the administration of fluids and electrolytes to the body, and during numerous other types of medical procedures and treatments. Such measurement and monitoring may be required on a fairly continuous basis or only at infrequent intervals, but in either case it is desirable that the measurement and monitoring be conducted as accurately as possible and with the least amount of physical discomfort to the patient.

There are also a variety of situations, both in vivo and in vitro, where it would be desirable to efficiently and accurately monitor or measure the concentration of biochemicals such as the concentration of the constituents of enzymatic systems including serum enzymes, glucose, lactic acid, pyruvic acid, creatinine, urea, etc., and the constituents of immunochemical systems. In all these situations, there is a need for miniaturizing the measuring apparatus and for improving the speed and reducing the cost of performing the measurements.

Detection, measurement and monitoring of chemical properties of a substance generally involves measurement of potential difference between two electrodes, with such potential difference being dependent upon the chemical activity being measured. Apparatus for performing such measurement, at least of ion activity, has typically included the use of glass electrodes having a hydrated glass layer. Such electrodes, however, are fairly limited as to the type of chemical properties which can be measured with only cation sensitive glass electrodes known to be presently available. See G. J. Moody and J. D. R. Thomas, *Selective Ion Sensitive Electrodes*, Merrow Publishing Co. Ltd., Watford, England, 1971.

Other prior art apparatus for measuring ion activity include solid state, homogeneous and heterogeneous electrodes and liquid ion exchanger memberane electrodes. See Moody and Thomas, supra. This apparatus is generally quite costly to construct, bulky and, as with glass electrodes, limited as to the types of electrochemical properties which it can measure.

A fairly recent development in apparatus for measuring ion activities is disclosed in "Development, Operation, and Application of the Ion-Sensitive Field-Effect Transistor as a Tool for Electrophysiology" by Piet Bergveld, IEEE Transactions of Biomedical Engineering, September, 1972, pages 342–351. Bergveld suggested the use of a metal oxide semiconductor Field-effect transistor (MOSFET) modified by removal of the gate metal, for measuring hydrogen and sodium ion activities in an aqueous solution. In particular, it was suggested that a MOSFET be constructed without the gate metal so that when the transistor were placed in an aqueous solution, the oxide (silicon dioxide) insulation layer would become hydrated and then, with the presence of impurities in the hydrated layer, ion selective. After hydration of the insulation layer of the MOSFET, the device, it was suggested, could be used for ion activity measurement by immersing the device in the solution in question and then recording conductivity changes of the device.

One problem with the device suggested by Bergveld is that immersion of the device is an aqueous solution results in continuation of the hydration process of the oxide insulation layer. Such a continuation of the hydration process would, of course, affect the accuracy of the ion activity measurements and, after a fairly short period of time, would result in shorting out the device, i.e., conduction through the device from the source electrode to the drain electrode would ultimately occur not through the conducting channel, but rather through the hydrated insulation layer.

An arrangement similar to that disclosed by Bergveld was described in "An Integrated Field-Effect Electrode for Bipotential Recording" by T. Matsuo and K. D. Wise, IEEE Transactions on Biomedical Engineering, November, 1974, pages 485–487. The device there disclosed, however, was designed for measuring biopotential differences and not for selectively measuring various chemical properties.

Another device of interest, designed to measure the concentration of various reducible gases, is disclosed in U.S. Pat. No. 3,719,564. This device comprises a solid-state electrochemical cell having a pair of electrodes and a rare earth fluoride electrolyte sandwiched therebetween. The concentration of certain reducible gases is measured by exposing the cell to a medium containing such gas and recording the cell current which, it has been determined, is a function of the concentration of the gas.

SUMMARY OF THE INVENTION

It is an object of the present invention to provide an improved field-effect transistor (FET) transducer for detecting and measuring chemical properties.

It is another object of the present invention to provide a compact, accurate, stable and yet inexpensive selective chemical sensitive FET transducer.

It is also an object of the present invention to provide such a transducer having a long life and which can be used in a variety of chemical measuring applications.

It is an additional object of the present invention to provide such a transducer which is suitable for both in vivo and in vitro applications.

It is a further object of the present invention, in accordance with one aspect thereof, to provide a structure which includes a plurality of such transducers, each adapted for simultaneously detecting and measuring different chemical properties.

It is still another object of the present invention, in accordance with another aspect thereof, to provide novel insertion systems for carrying and utilizing the transducer.

The above and other objects of the present invention are realized in an illustrative embodiment of a selective chemical sensitive FET transducer which includes a MOSFET type device in which the gate metal has been replaced by a chemical selective system adapted to interact with certain substances to which the device is exposed. Such interaction operates to develop an electrochemical potential in the selective system which modulates the electric field produced in the conducting channel of the device. The magnitude of this potential depends upon the extent of the interaction in the selective system which, in turn, generally depends upon the concentration of the interacting constituents. Variations in the electric field in the conducting channel of the device results in a variation in the conductance of the device and this latter variation can be readily measured to provide a measure of the chemical properties of the substances to which the transducer is exposed.

Advantageously, the transducer is encapsulated in a substance impervious material having an opening for exposing at least a portion of the selective system. The transducer is then utilized to detect chemical properties of a substance by exposing the transducer to the substance in question and noting variations in conductance of the transducer. A number of such transducers may be included on a single integrated circuit chip, each having a different selective system adapted to selectively interact with a different substance to which that system is exposed.

Chemical selective systems may be provided to measure different ion concentrations of solutions, to measure the concentration of various reducible gases, to measure concentrations of different enzymes or substrates of body fluids, and to measure the concentration of various antibodies and antigens.

In accordance with one aspect of the invention, a FET transducer of the type described is fixed in the lumen of a hollow needle near a tapered end thereof and is disposed so that solution entering the hollow at the tapered end will touch the exposed portion of the selective system of the transducer. Electrical conductors extend from the transducer through the needle lumen to carry signals to readout apparatus indicating conductance changes in the transducer.

BRIEF DESCRIPTION OF THE DRAWINGS

The above and other objects, features and advantages of the present invention will become apparent from a consideration of the following detailed description presented in connection with the accompanying drawings in which.

DETAILED DESCRIPTION

Figure 1:
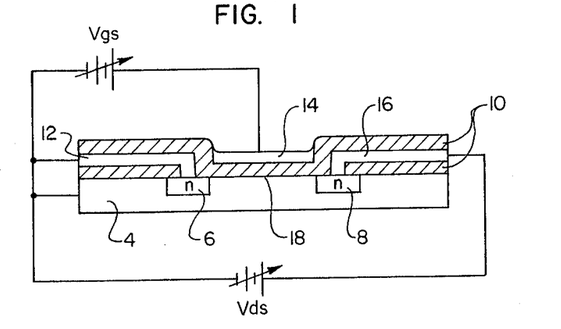
FIG. 1 is a cross-sectional view of a standard MOSFET device.

Before describing the present invention, it will be useful to briefly describe the operation of a standard MOSFET device. FIG. 1 is a cross-sectional view showing a MOSFET device and including a semiconductor substrate 4 which is typically silicon having a p-type doping polarity. Two spaced-apart diffusion regions 6 and 8 having an n-type doping polarity are located in the substance at the upper surface therof. One of the n-type diffusion regions is referred to as the source (in this case region 6) and the other is referred to as the drain (region 8 in FIG. 1). The surface region of the substrate 4 located between the two diffusion regions is commonly referred to as the gate region. Electrical insulator material 10, typically silicon dioxide or a silicon dioxide/silicon nitride sandwich, is thermally grown on the surface of the substrate 4 and in particular on the gate region between the diffusion regions 6 and 8. The insulator material between the two diffusion regions is known as the gate insulator. An electrically conductive material 12, 14 and 16, such as aluminum, is deposited on the source, gate and drain regions respectively to provide electrical contact with these portions of the MOSFET.

If the gate 14 is made positive with respect to the source 6, then holes in the substrate 14 will be repelled away from the substrate/insulator interface 18 and electrons will be attracted to the interface. This results in a so-called conducting channel being formed between the two diffusion regions 6 and 8 through which a current can be made to flow provided a potential difference exists between the two diffusion regions. The conductance of this channel and thus the magnitude of the current flow is dependent upon the magnitude of the charge at the substrate/insulator interface 18, i.e., upon the potential difference between the gate 14 and the source 6. In other words, the gate voltage controls the electron density and thus the current flow in the conducting channel and, alternatively, the magnitude of the current flow in the conducting channel provides an indication of the magnitude of the gate voltage. This latter feature is utilized in the present invention as will next be described.

Figure 2:
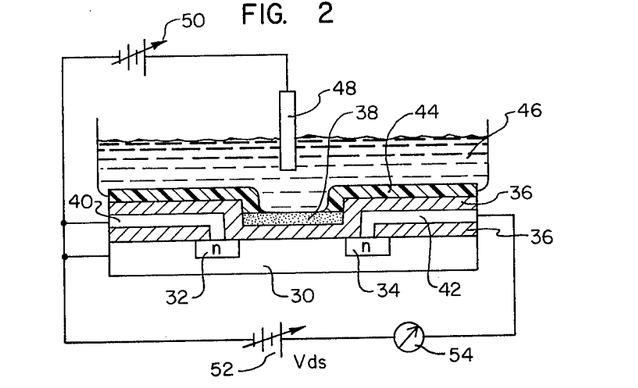
FIG. 2 shows a cross-sectional view of a chemical sensitive FET transducer made in accordance with the present invention and adapted for measuring ion activity or antibody/antigen concentration.

A cross-section of a selective chemical sensitive FET transducer made in accordance with the present invention is shown in FIG. 2. The transducer of FIG. 2 includes structure similar to that of FIG. 1 including a p-type silicon substrate 30, and two n-type regions 32 and 34 diffused into the surface of the substrate 30 to a depth, for example, of from one to two microns and spaced about twenty microns apart. The transducer also includes a thin layer of electrical insulator material 36, such as silicon dioxide, deposited over the substrate 30 and portions of the diffusion regions 32 and 34. Conductive layers 40 and 42 such as aluminum, n-type silicon, etc. are deposited respectively onto the source diffusion region 32 and the drain diffusion regions 34 to provide electrical contact therewith. The remaining circuitry of the FIG. 2 arrangement will be described momentarily.

The structure of FIG. 2, as thus far described, may be adapted to measure different ion activity, the concentration of certain reducible gases, the concentration of various enzymes or substrates, or the concentration antibodies or antigens. This would be done by providing an appropriate chemical selective system overlay on the insulator material 36 above the gate region of the transducer. Such a selective system would be adapted to interact with certain substances to which the system were exposed to thereby produce electrochemical potential changes in the system. These potential changes would operate to modulate the electric field produced in the conducting channel between the diffusion regions 32 and 34 and thus the conductance in the channel. Detection of conductance variation would thus enable detection and measurement of different chemical properties of a substance.

The FIG. 2 structure will be described specifically as it would be adapted to measure ion activity and antibody or antigen concentration. For ion activity measurement, a membrane 38 would be deposited over the insulator material 36 above the gate region of the transducer. The membrane 38 is adapted to selectively interact with a certain type of ion. That is, the membrane 38 includes an ion exchanger which allows a selective ion exchange between the exchanger and a solution to which the membrane is exposed. For example, the membrane 38 might be composed of an ion-exchanger such as calcium di-dodecylphosphate dissolved in a plasticizer such as di-octyladipate, all held in porous polyvinyl chloride. This specific membrane has been used to construct calcium selective electrodes. See Moody and Thomas, supra. Of course, membranes selective to different ions can also be fabricted using well known technology. See Moody and Thomas, supra and Rechnitz, G. A., "Membrane Bioprobe Electrodes", C & EN, January 27, 1975, page 29. Deposition of the membrane 38 on the insulator material 36 may be carried out simply by solution casting and may illustratively be of a thickness of about 5 microns.

Since the device of FIG. 2, when adapted for detection of ion activity, would typically be immersed in or exposed to solutions containing the ion in question, it is desirable that all except a portion of the membrane 38 be covered with some type of solution impervious material. Layer 44 of FIG. 2 represents such material and might, for example, comprise a polymerized epoxy resin. Although the layer 44 in FIG. 2 is only shown as covering the insulator material 36 and a portion of the membrane 38, it should be understood that the solution impervious material would cover all parts of the device including electrical leads, etc., which might be immersed in the solution. The type of solution impervious material used, of course, would depend upon the kinds of solution into which the transducer was to be immersed, but generally, the material should be at least water impervious and preferably biocompatible, i.e., should not adversely interact with the solution or tissue to which the device is exposed.

A solution into which the transducer of FIG. 2 would be immersed is represented diagrammatically and identified by numeral 46, and is shown as being in contact only with the solution impervious layer 44 and the membrane 38. A silver/silver chloride, calomel or other suitable reference electrode 48 is provided to establish a reference voltage for operation of the transducer. The reference electrode 48 is coupled to a voltage source 50 which develops the desired reference voltage. A voltage source 52 is also provided between the source electrode 40 and drain electrode 42 to establish a potential difference sufficient to cause current flow in the conducting channel between diffusion regions 32 and 34. An ammeter 54 is coupled in circuit between the voltage source 52 and the drain electrode 42 for measuring the drain current.

When the tranducer of FIG. 2 is exposed to a solution 46 containing ion which will interact with the membrane 38, the transducer operates in a fashion similar to the MOSFET shown in FIG. 1. That is, when the reference electrode 48 is properly biased, ions in the solution 46 interact with the ion selective membrane 38 to create a potential difference between the membrane and the solution. This creates an electric field in the conducting channel and the strength of this field, which is dependent upon the concentration of ions in the solution, controls the magnitude of current flow through the conducting channel and thus the magnitude of the drain current. The drain current is measured by the ammeter 54 which thus provides a measure of the ion concentration in the solution 46.

The membrane 38, in addition to being composed of polyvinyl chloride and an appropriate ion exchanger, may also be composed of polyurethane, silicone rubber or a variety of other neutral, hydrophobic matrices into which is dissolved an appropriate ion exchanger. See Moody and Thomas, supra. Solid-state or crystal ionic conductive membranes of the type described, for example, in the aforecited Rechnitz reference could also be utilized and would be applied over the insulator material 36, for example, by vacuum deposition.

For measuring immunochemical activities--antibody or anitgen concentration--, the transducer arrangement of FIG. 2 might include a membrane 38 comprising a hydrophobic polymer, such as polyvinyl chloride or polystyrene, with an antibody (or antigen) covalently bound to the surface thereof. A method of performing such binding is disclosed in copending patent application, Ser. No. 506,464, filed Sept. 16, 1974. Such a membrane is deposited over the insulator material 36 using standard thin-film deposition techniques such as solution casting and might illustratively be of a thickness of about 20 microns.

When a transducer having such a membrane is exposed to a solution containing an antigen with which the antibody bound to the surface of the membrane may complex (or antibody with which the antigen bound to the surface of the membrane may complex), the surface potential of the membrane changes as a result of the immunochemical reaction of antigen complexing with the membrane antibody (or antibody complexing with the membrane antigen). This reaction is described in the aforecited copending application. The change in surface potential, which depends on the concentration of antigen (or antibody) in the solution, modulates the electric field in the conducting channel between diffusion regions 32 and 34 to thereby vary the conductance of the transducer. In this manner, the concentration of different antibodies and antigens in a solution may be simply and accurately measured.

Figure 3:
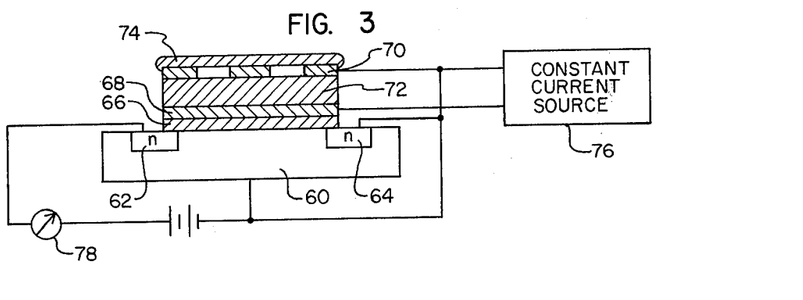
FIG. 3 is a cross-sectional view of a chemical sensitive FET transducer adapted for measuring concentration of reducible gases.

FIG. 3 shows a chemical sensitive FET transducer which may be used for measuring reducible gas concentrations. This transducer includes a p-type silicon substrate 60 and two spaced-apart n-type diffusion regions 62 and 64. In this case, the diffusion region 62 is the drain and the diffusion region 64 is the source. Deposited over the gate region of the substrate 60 is a silicon dioxide insulator layer 66. Placed in contact with the insulator layer 66 is an electrochemical cell including a thin film anode (or cathode) 68 which is spaced apart from a thin film cathode (or anode) grid 70. Sandwiched between the anode 68 and cathode grid 70 is a rare earth fluoride electrolyte 72 such as lanthanum fluoride. Deposited over the cathode grid 70 is a reducible gas selective membrane 74. The membrane 74 is adapted to selectively pass certain reducible gases which, as will be mentioned shortly, it is desired that the apparatus of FIG. 3 detect. If, for example, oxygen is to be sensed, the membrane 74 may be comprised of polyethylene. The configuration of the anode 68, cathode 70, electrolyte 72 and membrane 74 is fully described in A. C. Lilly, Jr. et al, U.S. Pat. No. 3,719,564 which discusses the use of such structure fabricated on a ceramic substrte for measuring the concentration of reducible gases. As set forth in the Lilly patent, the cathode 70 could be comprised of a noble metal and the anode 68 could be comprised of a metal alike or different from the cathode metal. A variety of suitable rare earth fluoride electrolytes are also discussed in the patent. The cathode and anode may be applied to the transducer by vacuum deposition techniques and the electrolyte may be applied by RF sputtering techniques, all well known.

Referring again to FIG. 3, a constant current dc or ac source 76 is coupled to the anode 68 and cathode 70 to polarize the electrodes so that any variation in the voltage between the electrodes will be the result of the interaction of reducible gas with the cell electrolyte 72 as hereafter discussed.

In operation, the concentration of reducible gas to which the FIG. 3 apparatus is exposed is measured by again ascertaining the drain current of the FET by an ammeter 78. Specifically, the voltage drop between the cathode 70 and anode 68 is a function of the concentration of reducible gas and this voltage determines the magnitude of the electric field created in the conducting channel located between the two diffusion regions 62 and 64. That is, as the concentration of reducible gas increases, the polarization voltage of the cathode decreases. Thus, as the concentration of reducible gas is increased, the voltage between the cathode 70 and anode 68 drops, thereby reducing the electric field in the conducting channel and this, in turn, results in a decrease in the drain current. Measuring the drain current by the ammeter 78 thus provides an indication of the concentration of the reducible gas being measured.

The arrangement of FIG. 3 gives the advantage of "on site" amplification of signals produced in response to variations in the voltage between the cathode and anode of the electrochemical cell. That is, the structure of the electrochemical cell and FET can be produced on a single chip as shown in FIG. 3 and this combination is highly sensitive and stable and has desirable signal to noise properties.

Figure 4A:
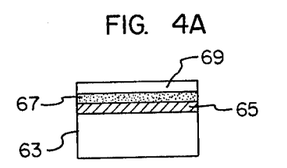
FIGS. 4A and 4B show cross-sectional views of chemical sensitive FET transducers adapted for measuring enzyme/substrate concentration.
Figure 4B:
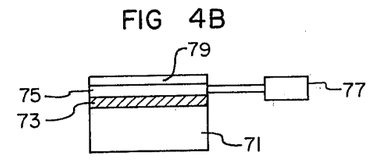

Two illustrative embodiments of the present invention adapted to measure enzyme or substrate concentration are diagrammatically shown in FIGS. 4A and 4B. The structure of FIG. 4A includes a p-type substrate and n-type diffusion regions (both represented by block 63), just as the previously described structures, and electrical insulator material 65 overlying the substrate and diffusion regions. An ion selective membrane 67, of the type previously described, overlies the insulator material 65. As thus far described, the structure of FIG. 4A is the same as that of FIG. 2. The difference between the two is that the FIG. 4A structure further includes a thin film layer or membrane 69 overlying the ion selective membrane 67. The membrane 69 is composed of a base material such as a water-based gel (agar, polyvinyl alcohol, etc.) having either an enzyme or substrate immobilized therein. If the membrane contains an immmobilized enzyme, then the transducer of FIG. 4A can detect and measure concentration of substrates with which the enzyme may react. If the membrane contains an immobilized substrate, then the transducer can detect and measure concentrations of enzymes with which the substrate may react. The membrane 69 may be placed over the ion selective membrane 67 by solution casting and may illustratively be of a thickness of 20 microns.

When the membrane 69 containing a certain immobilized enzyme is exposed to a solution containing a substrate with which the enzyme will react, the substrate diffuses into the membrane where the enzyme catalyzes conversion of the substrate into a product and this conversion either yields or consumes ions. The change in ion concentration is then detected, as previously described, by the remaining structure of the FIG. 4A transducer. A corresponding reaction occurs when the membrane 69 containing certain immobilized substrates is exposed to a solution containing an enzyme with which the substrates may react. In either case, the catalyzed reactions result in either an increase or decrease in the concentration of ions with which the ion selective membrane 67 may react. Since the magnitude of the ion concentration change depends upon the amount of substrate or enzyme being converted or reacted, a measure of the ion concentration change provides a measure of the concentration of substrate or enzyme being converted.

Enzyme and substrate specific membranes suitable for use in the FIG. 4A transducer have been described in Gough, D. A. and Andrade, J. D. , "Enzyme Electrodes", Science 18D, 380 (1973) and the literature cited therein. An exemplary membrane is acrylamide gel containing immobilized beta glucosidase which, when exposed to a solution containing amygdalin, causes production of glucose, benzaldehyde and the ion $CN^-$. This ion would react with a solid state ion selective membrane 67 composed of silver sulfide/silver iodide mixture to modulate the electric field in the FET 63 and thereby provide an indication of the concentration of amygdalin in the solution. See G. A. Rechnitz and R. Llenado, "Enzyme Electrode For Amygdalin", Anal. Chem., Vol. 43, 1971 p. 283. It is to be understood, of course, that only certain enzymes and substrates will react to either consume or produce ions and these are the enzymes and substrates which would be utilized with the FIG. 4A configuration.

FIG. 4B shows an alternative embodiment of a transducer adapted to detect enzyme or substrate concentrations. The FIG. 4B structure includes a FET having p-type and n-type regions 71 and electrical insulator material 73 as in the previously described transducers. An electrochemical cell 75, including a constant current source 77, overlies the insulator material 73 in the manner already discussed in conjunction with FIG. 3.

An enzyme or substrate selective layer or membrane 79 overlies the electrochemical cell 75.

The membrane 79 is composed of a base material, such as a water-based gel, containing an immobilized enzyme or substrate which will react with a corresponding substrate or enzyme respectively to produce or consume a reducible gas. Such production or consumption of reducible gas affects the concentration of such reducible gas reaching and reacting with the electrochemical cell 75 and this, in turn, affects the magnitude of the electric field produced in the FET 71 and previously described. Thus, a measure of the concentration of an enzyme or substrate in a solution may be made by exposing the transducer of FIG. 4B to the solution and noting the variation in the conductance of FET.

An exemplary membrane 79 is composed of agar containing any immobilized oxidase such lactate oxidase or glucose oxidase. When such membrane is exposed, in the presence of oxygen, to a solution containing oxidizable substrate, such as lactate or glucose, the oxidase, substrate and oxygen react to produce $CO_2$ and $H_2O$. Because the reducible gas oxygen is consumed in the reaction (the amount consumed dependent upon the concentration of lactates in the solution), the concentration of oxygen reaching and reacting with the electrochemical cell 75 is reduced and this operates to vary the voltage between cell electrodes and thus the electric filed produced in the FET 71.

Figure 5A:
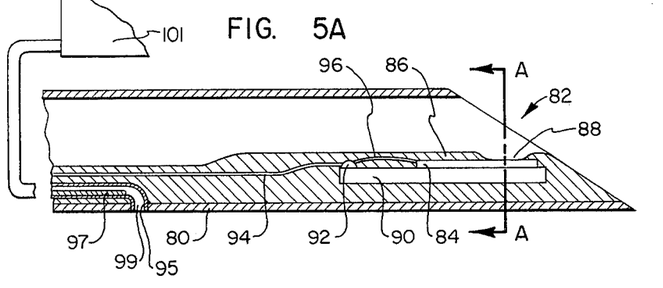
FIGS. 5A and 5B show a side cross-sectional view and an end cross-sectional view respectively of a needle and transducer for use in measuring chemical properties of a substance.
Figure 5B:
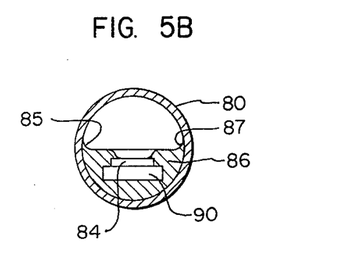

FIGS. 5a and 5B show one embodiment of an insertion device utilizing the transducer of the present invention. FIG. 5A is a side cross-sectional view of the device, and FIG. 5B is a front cross-sectional view taken along line A--A of FIG. 5A. Referring to FIG. 5A, there is shown a needle-tip insertion device including a hollow needle 80, one end 82 of which is beveled to enable insertion of the needle in animal tissue and the like. Disposed in the needle luman near the beveled end is a FET transducer 84 constructed as earlier described with a chemical selective system (not shown in FIG. 5A) positioned over the gate region of the FET. The transducer 84 is mounted on a support substrate 90 on which are deposited bonding pads 92 to which conducting wires 94 are coupled. Bonding wires 96 connects the conducting wires 94 to the transducer 84. The transducer 84 and associated components are encapsulated in a solution impervious material 86 having an opening 88 for exposing the selective system of the transducer.

The conductors 94 extend proximally in the lumen of the needle and in the encapsulation material 86 to a point (not shown) where they would exit from the needle for coupling to a power source and some type of readout apparatus such as an ammeter. The transducer 84 is disposed in the lumen of the needle so that the opening 88 in the solution impervious material 86 faces inwardly of the needle 80 and so that extracellular fluid, blood, etc., from tissue into which the needle is inserted will bathe the selective system of the transducer. The encapsulation material 86 may be held in place within the needle by appropriate solution impervious material such as medical grade silastic adhesive.

In placing the transducer in the lumen of the needle 80, it is important that the exposed surface area of the solution impervious material 86 be generally smooth and not include pockets or cavities where the solution being measured might collect and remain. When the solution in question is blood, this is especially important since blood would tend to clot and possibly clog the transducer and needle openings if pockets or cavities were present. For this reason, at points where the solution impervious material 86 joins the needle wall, such as at 85 and 87 (FIG. 5B), the material 86 is formed to present a rounded valley as shown. Also, the surface of the solution impervious material 86 is formed to be generally contiguous with the plane defined by the beveled end of the needle. Forming the solution impervious material 86 in this manner facilitates insertion of the needle in animal tissue.

A reference electrode is provided for the transducer/needle arrangement of FIGS. 5A and 5B by including an electrode 97 disposed in an electrical insulative tube 95 which in turn is disposed in the lumen of the needle 80. One end of the tube 95 in an opening 99 in the side wall of the needle 80 so that the interior of the tube communicates through the opening to the exterior of the needle. The other end of the tube 95 extends proximally in the lumen of the needle to a point where it exits from the needle and is coupled to a source 101 of electrolytic solution such as potassium chloride. The reference electrode 97 is recessed in the tube 95 a short distance from the opening 99 and is coupled to a reference voltage source such as the source 50 shown in FIG. 2. The electrolytic solution source 101 is adapted to supply a slow drip of solution to the tube 95 to establish a conductive interface between the reference electrode 97 and animal tissue into which the needle 80 may be inserted. It is apparent that a variety of reference electrode configurations could be provided with the transducer/needle arrangement of FIGS. 5A and 5B, with the configuration shown being one illustrative approach.

Advantageously, the proximal end of the needle 80 is coupled to a syringe in any well known fashion and the needle may then be forced into animal tissue and the syringe operated to withdraw or inject solution. Of course, the needle might be coupled to any of a variety of other instruments for applying solution to the transducer to calibrate the transducer or facilitate measurement of chemical properties of the solution.

Figure 6A:
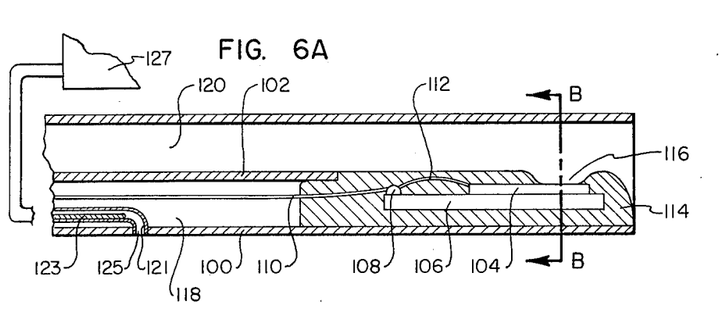
FIGS. 6A and 6B show a side cross-sectional view and an end cross-sectional view respectively of a split-lumen catheter and transducer for use in measuring chemical properties of a substance.
Figure 6B:
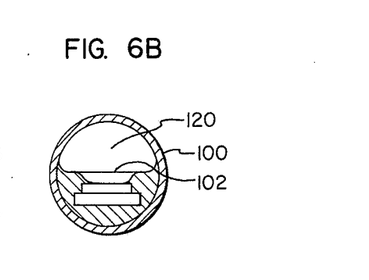

FIGS. 6A and 6B show another embodiment of an insertion device containing the transducer of the present invention. FIG. 6A shows a side cross-sectional view of the device and FIG. 6B shows a front cross-sectional view taken along line B—B of FIG. 6A. The insertion device of FIG. 6A is a split-lumen catheter comprising a tubular member 100 having a center wall 102 extending from near one end of the catheter to the other end thereof and dividing the tubular member 100 into two sections defining separate lumens 118 and 120. In one of the lumens 118 is disposed a transducer 104 mounted on a support substrate 106. Bonding pads 108 couple conductors 110 to bonding leads 112 which, in turn, are connected to the transducer 104. The conductors 110 extend from bonding pads 108 through lumen 118 to the proximal end of the catheter where they exit from catheter for connection to signal processing circuitry.

The transducer 104 and associated components are encapsulated in a solution impervious material 114 in a manner similar to that for the arrangement of FIGS. 5A and 5B. An opening 116 is provided in the solution impervious material 114 to expose the chemical selective system of the transducer 104. The solution impervious material 114 containing the transducer 104 is fixed in the catheter with solution impervious adhesive in a manner to completely seal the lumen 118 from the other lumen 120. (See FIG. 6B) as with the arrangement of FIGS. 5A and 5B the solution impervious material 114 is formed in the catheter to present rounded valleys so that the solution being measured will not readily collect and clot in the catheter.

As seen in FIG. 6A, the transducer 104 is positioned so that fluid entering lumen 120 will touch the chemical selective system of the transducer to thereby enable measurement of chemical properties of the fluid. The end of the catheter opposite that in which the transducer is fixed could advantageously be coupled to a syringe for drawing or forcing fluids past the transducer through lumen 120 or simply for washing and cleaning the catheter.

A reference electrode 123 contained in an electrical insulative tube 121 is provided in the catheter in a manner similar to that for the needle of FIGS. 5A and 5B. The tube 121 is coupled to an electrolytic solution source 127 as discussed for the FIGS. 5A and 5B structure.

Figure 7:
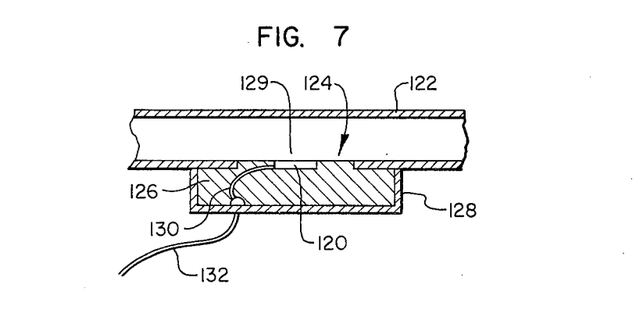
FIG. 7 shows a side cross-sectional view of a hollow tube and transducer for use in measuring chemical properties of a solution passing through the tube.

FIG. 7 shows still another embodiment of an arrangement for exposing a transducer 120 to solutions whose chemical properties are to be measured. This arrangement includes a tube 122 having an opening 124 in one side thereof over which is fixed the transducer 120. The transducer 120 is encapsulated in a solution impervious material 126 which is contained in a housing 128 attached to the side of the tube 122. An opening 129 in the solution impervious material exposes the chemical selective system of the transducer 120. The transducer 120 is coupled by bonding wires 130 to conductors 132 for carrying signals to some type of readout device. The opening 124 in the side of the tube 122 is completely filled with the solution impervious material 126 and housing 128 so that no fluid carried by the tube 122 will leak therefrom. As can be seen from FIG. 7, solution passing in either direction in the tube 122 will touch the transducer, and in particular, the chemical selective system of the transducer, to give a readout. A reference electrode, separate from the FIG. 7 structure, could be utilized as previously described.

Figure 8:
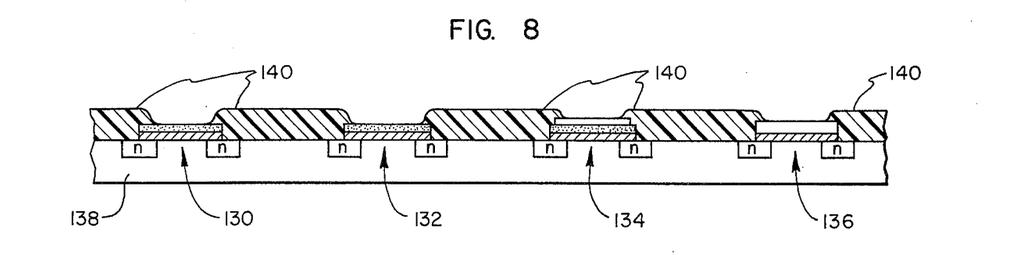
FIG. 8 shows a cross-sectional view of an integrated circuit chip including a plurality of transducers for measuring chemical properties of a substance.

FIG. 8 shows a plurality of transducers 130 through 136 constructed on a p-type substrate 138. Each transducer, of course, includes a pair of n-type diffusion regions overlayed by a suitable insulator layer. Transducers 130 and 132 further include selective membrane layers respectively adapted to interact with a certain ion and of a certain antibody or antigen. Transducer 134 includes a chemical selective system adapted to interact with a certain enzyme or substrate and transducer 136 includes the combination of a cathode, electroyte, anode and gas selective membrane adapted to interact with a certain reducible gas. A solution and gas impervious material 140 is disposed over the surface of the substrate 138 and over each transducer except for openings which expose a portion of the chemical selective systems of each transducer. Each transducer 130 through 136 would be coupled to appropriate voltage sources and readout devices to enable the transducers to operate as previously described.

By providing a plurality of transducers on a single integrated circuit chip, independent but simultaneous readings can be made of the chemical properties of a solution or gas to which the chip is exposed. Such a chip could be fixed in a needle, catheter or tube as previously described as well as a variety of other arrangements for simultaneously exposing the transducers on the chip to various solutions or gases being measured.

In the manner shown and described, an inexpensive, simple to construct and yet rugged chemical sensitive FET transducer may be provided. The transducer provides on-site amplification of the signals produced in response to detected chemical properties. The arrangement is compact, long-lived and versatile and may be easily adapted for use with a variety of insertion devices.

It is to be understood that the above-described arrangements are only illustrative of the application of the principles of the present invention. Numerous other modifications and alternative arrangements may be devised by those skilled in the art without departing from the spirit and scope of the present invention and the appended claims are intended to cover such modifications and arrangements.

What is claimed is:

1. A chemical sensitive field-effect transistor transducer unit for detecting chemical properties of substances to which the unit is exposed and including a transducer which comprises:
   a semi-conductor substrate having a doping polarity,
   a pair of spaced apart diffusion regions located at the surface of said substrate material,
   an electrical insulator material overlying at least a portion of said diffusion regions and the surface of the substrate material lying between the diffusion regions,
   a chemical selective system containing a chemical selective membrane overlying said insulator material, and
   a reference electrode connected to circuit relationship with said spaced apart diffusion regions through a potential source such that a potential is created and added to the potential generated in the chemical selective membrane the combination of which affects the conductivity between said diffusion regions as a measure of the chemical properties of said substances.

2. A transducer unit as in claim 1 wherein said selective system comprises a first membrane adapted to selectively react with certain ions when exposed to a substance containing such ions.

3. A transducer unit as in claim 2 wherein said membrane is composed of polyvinyl chloride and an ion-exchanger contained therein.

4. A transducer unit as in claim 2 wherein said membrane is composed of polyurethane and an ion-exchanger contained therein.

5. A transducer unit as in claim 2 wherein said membrane is composed of silicone rubber and an ion-exchanger contained therein.

6. A transducer unit as in claim 2 wherein said membrane is composed of a solid state ionic conductor of generally low water solubility.

7. A transducer unit as in claim 2 wherein said selective system further comprises a second membrane overlying said first membrane and having an enzyme immobilized therein so that when the second membrane is exposed to a substance containing a substrate with which enzyme may react, the enzyme reacts with the substrate to yield ions capable of interacting with said first membrane.

8. A transducer unit as in claim 2 wherein said selective system further comprises a second membrane and having a substrate immobilized therein so that when the second membrane is exposed to a substance containing an enzyme with which the substrate may react, the substrate reacts with the enzyme to yield ions capable of interacting with said first membrane.

9. A transducer unit as in claim 1 wherein said selective system comprises a membrane having a certain antibody covalently bound to the surface thereof so that when the membrane is exposed to a substance containing a corresponding antigen, the antibody complexes with the antigen to change the potential at the surface of the membrane, said potential change thereby changing the electric field in the substrate material.

10. A transducer unit as in claim 1 wherein said selective system comprises a membrane having a certain antigen covalently bound to the surface thereof so that when the membrane is exposed to a substance containing a corresponding antibody, the antigen complexes with the antibody to change the potential at the surface of the membrane, said potential change thereby changing the electric field in the substrate material.

11. A transducer unit as in claim 1 wherein said transducer further comprises a substance impervious material disposed about said substrate material, diffusion regions, insulator material and membrane and including an opening for exposing a portion of said selective system.

12. A hollow needle, one end of which is tapered to facilitate insertion thereof in animal tissue comprising the transducer unit of claim 11, said transducer unit being fixed in the lumen of the needle near the tapered end so that the portion of the selective system exposed through the opening in the substance impervious material is exposed to fluid entering the lumen, and electrical conductors coupled to said diffusion regions and said substrate material and extending through the substance impervious material and through the lumen of the needle toward the end opposite the tapered end.

13. A hollow needle as in claim 12 wherein said transducer is fixed within the needle lumen by a substance impervious adhesive and said conductors are encapsulated in and bonded to the wall of the needle by a substance impervious adhesive, and wherein the substance impervious material and substance impervious adhesive are formed to present a surface area which is substantially coincident with the opening at the tapered end of the needle.

14. A hollow needle as in claim 12 wherein said needle includes an opening in the side thereof, and wherein said transducer unit further comprises
an electrical insulative tube disposed in the needle lumen with one end of the tube fixed in the side opening of the needle to enable the tube interior to communicate through the opening and the other end extending toward the end of the needle opposite the tapered end.

15. A hollow unit as in claim 14 further comprising means for supplying an electrolytic solution to said insulative tube.

16. A split-lumen catheter having a center wall extending substantially the length of the catheter to define two lumens, comprising the transducer unit of claim 11, said transducer being fixed in one of the lumens near one end of the catheter so that the portion of the selective system exposed through the opening in the substance impervious material is exposed to fluid entering the other lumen, and electrical conductors coupled to said diffusion regions and said substrate material and extending through the substance impervious material and through one lumen toward the other end of the catheter.

17. A catheter as in claim 16 wherein said transducer is fixed within said one lumen by a substance impervious adhesive so that the transducer and substance impervious adhesive seal said one lumen from the other lumen.

18. A catheter as in claim 16 wherein said catheter includes an opening in the exterior wall surrounding said one lumen, and wherein said transducer unit further comprises
an electrical insulative tube disposed in said one lumen with one end of the tube fixed in the exterior wall opening to enable the tube interior to communicate through the opening and the other end of the tube extending toward said other end of the catheter.

19. A catheter as in claim 18 further comprising means for supplying an electrolytic solution to said insulative tube.

20. A transducer unit as in claim 11 further comprising a tube for carrying fluids, said tube having an opening in a side wall thereof, said transducer being mounted on the outside of the tube over the opening so that the portion of the selective system exposed through the opening in the substance impervious material is also exposed through the opening in the tube to fluids passing through the tube.

21. A chemical sensitive field-effect transistor transducer for detecting different chemical properties of a substance comprising:
a semi-conductor substrate material having a doping polarity,
a plurality of pairs of spaced apart diffusion regions located at the surface of said substrate and having a doping polarity opposite that of the substrate material.
electrical insulator material overlying at least portions of each diffusion region and the surface of the substrate material lying between each pair of diffusion regions,
a plurality of chemical selective systems, each containing a chemical selective membrane overlying the insulator material covering a different pair of diffusion regions and the substrate surface lying therebetween, and
a reference electrode connected in circuit relationship with each pair of spaced apart diffusion regions through a potential source such that a potential is created and added to the potential generated in each chemical selective membrane the combination of which affects the conductivity between each pair of diffusion regions as a measure of the chemical property of said substance being detected at each pair of diffusion regions.

22. A transducer as in claim 21 further comprising a substance impervious material disposed over said substrate material, diffused regions, insulator material and selective systems, and including a plurality of openings, each exposing a portion of a different one of said selective systems.

23. Apparatus for determining the chemical properties of substances including the transducer of claim 22 and a hollow needle tapered at one end to facilitate insertion thereof in animal tissue, said transducer being fixed in the hollow of the needle near the tapered end so that the portions of the selective systems exposed through the openings in the substance impervious material are exposed to fluids entereing the needle hollow.

24. Apparatus for determining the chemical properties of substances including the transducer of claim 22 and a split-lumen catheter having a center wall defining two lumens within the catheter, said transducer being fixed in a first lumen near one end of the catheter so that the portions of the selective systems exposed through the openings in the substance impervious material are exposed to fluids entering the other lumen.

25. A chemical sensitive field-effect transistor transducer unit for detecting chemical properties of substances to which the unit is exposed and including a transducer which comprises:
   a semi-conductor substrate having a doping polarity,
   a pair of spaced apart diffusion regions located at the surface of said substrate material,
   an electrical insulator material overlying at least a portion of said diffusion regions and the surface of the substrate material lying between the diffusion regions,
   a chemical selective system comprising:
      a pair of electrodes, one of which is positioned in contacting relation to the insulated material,
      a solid rare earth fluoride electrolyte material disposed between and maintained in contact with the electrodes,
      a constant current source coupled between said electrodes to polarize the electrodes,
      a selective first membrane overlying the other electrode not in contacting relation to the insulator material, and adapted to selectively pass certain reducible gases when exposed to a gas containing such reducible gases
      said constant current source being connected in circuit relationship with said spaced apart diffusion regions such that a potential is created and added to the potential generated between the electrodes by the reducible gases the combination of which affects the conductivity between said diffusion regions as a measure of the concentration of the reducible gases.

26. A transducer unit as in Claim 25 wherein said selective system further comprises a second membrane overlying said first membrane and having an enzyme immobilized therein so that when the second membrane is exposed, in the presence of said certain reducible gases, to a substance containing a substrate with which the enzyme may react, the enzyme reacts with the substrate and reducible gases to thereby affect the concentration of reducible gases passing through said first membrane.

27. A transducer unit as in Claim 25 wherein said selective system further comprises a second membrane overlying said first membrane and having a substrate immobilized therein so that when the second membrane is exposed, in the presence of said certain reducible gases, to a substance containing an enzyme with which the substrate may react, the substrate reacts with the enzyme and reducible gases to thereby affect the concentration of reducible gases passing through said first membrane.

* * * * *

REEXAMINATION CERTIFICATE (240th)
United States Patent [19]
Johnson et al.

[11] B1 4,020,830

[45] Certificate Issued Sep. 4, 1984

[54] SELECTIVE CHEMICAL SENSITIVE FET TRANSDUCERS

[75] Inventors: Curtis C. Johnson, Sandy; Stanley D. Moss, Kaysville; Jiri A. Janata, Salt Lake City, all of Utah

[73] Assignee: The University of Utah, Salt Lake City, Utah

Reexamination Request:
No. 90/000,395, Jun. 6, 1983

Reexamination Certificate for:
| | |
|---|---|
| Patent No.: | 4,020,830 |
| Issued: | May 3, 1977 |
| Appl. No.: | 557,545 |
| Filed: | Mar. 12, 1975 |

[51] Int. Cl.$^3$ .................. A61B 5/05; C12Q 1/00; G01N 27/46

[52] U.S. Cl. ................... 128/635; 204/403; 204/412; 204/414; 204/415; 204/418; 204/425; 204/426; 324/425; 357/23; 357/25; 357/26; 357/54; 435/291

[58] Field of Search .................. 357/25; 128/635; 204/403, 406, 412, 416

[56] References Cited

U.S. PATENT DOCUMENTS

| | | | |
|---|---|---|---|
| 3,049,118 | 8/1962 | Arthur et al. | 128/635 |
| 3,498,289 | 3/1970 | Watanabe et al. | 128/635 |
| 3,605,722 | 9/1971 | Riseman et al. | 128/635 |
| 3,682,159 | 8/1972 | Imredy et al. | 128/635 |
| 3,719,564 | 3/1973 | Lilly et al. | 204/1 T |
| 3,831,432 | 8/1974 | Cox | 73/23 |

OTHER PUBLICATIONS

12th Conference of the Medical Engineering Society of Japan Compendium of Scheduled Addresses, May 1973.
Documentary Materials for Research Meeting on Electrical Measurement-Documents No. EM-74-22 through 31, "New Fields of Instrumentation, v. Bio-Electrical Instrumentation, Jan. 28, 29, 1974, Japan.
Moody et al, "Selective Ion Sensitive Electrodes", Merrow Technical Library, 1971.
Fiedler et al, "Selectrode-The Universal Ion-Selective Electrode", Part VII, A Valinomycin-Based Potassium Electrode with Nonporous Polymer Membrane and Solid-State Inner Reference System Analytica Chimica Acta. 67, (1973), 179-193.
Castillo et al, "Lipid Films as Transducers for Detection of Antigen-Antibody and Enzyme-Substrate Reactions", Science, vol. 153, pp. 185-188.
Gough et al, "Enzyme Electrodes", Science, vol. 180, pp. 380-384.
Bergveld, "Development, Operation, and Application of the Ion-Sensitive Field-Effect Transistor as a Tool for Electrophysiology", IEEE Transactions on Biomedical Engineering, vol. BME-19, No. 5, Sep. 1972.

*Primary Examiner*—Gerald L. Kaplan

[57] ABSTRACT

A chemical sensitive field-effect transistor transducer capable of selectively detecting and measuring chemical properties of substances to which the transducer is exposed. The transducer includes a semiconductor substrate material having a certain doping polarity, a pair of spaced apart diffusion regions located at the surface of the substrate material and having a doping polarity opposite that of the substrate material, electrical insulator material overlying the diffusion regions and the surface of the substrate material lying between the diffusion regions, and a chemical selective system overlying the insulator material. The chemical selective system is adapted to interact with certain substances and thereby modulate an electric field produced in the substrate material between the diffusion regions. This modulation is dependent upon the chemical properties of the substances and provides a measure of those chemical properties. The chemical selective system may include various structures for measuring ion activity, immunochemical concentrations, reducible gas concentrations and the concentrations of enzymes and substrates.

REEXAMINATION CERTIFICATE ISSUED UNDER 35 U.S.C. 307.

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 5, lines 6-22:
The structure of FIG. 2, as thus far described, may be adapted to measure different ion activity, the concentration of certain reducible gases, *or the concentration of various enzymes or substrates* [, or the concentration]. [antibodies or antigens.] This would be done by providing an appropriate chemical selective system overlay on the insulator material 36 above the gate region of the transducer. Such a selective system would be adapted to interact with certain substances to which the system were exposed to thereby produce electrochemical potential changes in the system. These potential changes would operate to modulate the electric field produced in the conducting channel between the diffusion regions 32 and 34 and thus the conductance in the channel. Detection of conductance variation would thus enable detection and measurement of different chemical properties of a substance.

AS A RESULT OF REEXAMINATION, IT HAS BEEN DETERMINED THAT:

Claims 2, 9-11 and 25-27 are cancelled.

Claims 1, 3-8 and 12-21 are determined to be patentable as amended.

Claims 22-24, dependent on an amended claim, are determined to be patentable.

1. A chemical sensitive field-effect transistor transducer unit for detecting chemical properties of substances to which the unit is exposed and including a transducer which comprises:
   a semi-conductor substrate having a doping polarity,
   a pair of spaced apart diffusion regions located at the surface of said substrate material,
   an electrical insulator material overlying at least a portion of said diffusion regions and the surface of the substrate material lying between the diffusion regions,
   a chemical selective system [containing a] *which includes a first* chemical selective membrane overlying said insulator material *and containing an ion-exchanger which selectively reacts with certain ions when exposed to substances containing such ions to enable an exchange of ions between the ion-exchanger and the substances,* and
   a reference electrode connected [to] *in* circuit relationship with said spaced apart diffusion regions through a potential source such that a potential is created and added to the potential generated in the chemical selective membrane, the combination of which affects the conductivity between said diffusion regions as a measure of the chemical properties of said substances.

3. A transducer unit as in claim [2] *1* wherein said membrane is composed of polyvinyl chloride and an ion-exchanger contained therein.

4. A transducer unit as in claim [2] *1* wherein said membrane is composed of polyurethane and an ion-exchanger contained therein.

5. A transducer unit as in claim [2] *1* wherein said membrane is composed of silicone rubber and an ion-exchanger contained therein.

6. A transducer unit as in claim [2] *1* wherein said membrane is composed of a solid state ionic conductor of generally low water solubility.

7. A transducer unit as in claim [2] *1* wherein said selective system further comprises a second membrane overlying said first membrane and having an enzyme immobilized therein so that when the second membrane is exposed to a substance containing a substrate with which enzyme may react, the enzyme reacts with the substrate to yield ions capable of interacting with said first membrane.

8. A transducer unit as in claim [2] *1* wherein said selective system further comprises a second membrane and having a substrate immobilized therein so that when the second membrane is exposed to a substance containing an enzyme with which the substrate may react, the substrate reacts with the enzyme to yield ions capable of interacting with said first membrane.

12. *A chemical sensitive device for detecting chemical properties of substances to which the device is exposed comprising*
   [A] *a* hollow needle, one end of which is tapered to facilitate insertion thereof in animal tissue [comprising the],
   *a* transducer unit [of claim 11] *including*
      *a semi-conductor substrate having a doping polarity,*
      *a pair of spaced apart diffusion regions located at the surface of said substrate material,*
      *an electrical insulator material overlying at least a portion of said diffusion regions and the surface of the substrate material lying between the diffusion regions,*
      *a chemical selective system adapted to interact with said substances and containing a chemical selective membrane overlying said insulator material,*
      *a reference electrode connected in circuit relationship with said spaced apart diffusion regions through a potential source such that a potential is created and added to the potential generated in the chemical selective membrane the combination of which affects the conductivity between said diffusion regions as a measure of the chemical properties of said substances, and*
      *a substance impervious material disposed about said substrate material, diffusion regions, insulator material and membrane and including an opening for exposing a portion of said selective system,*
   said transducer unit being fixed in the lumen of the needle near the tapered end so that the portion of the selective system exposed through the opening in the substance impervious material is exposed to fluid entering the lumen, and
   electrical conductors coupled to said diffusion regions and said substrate material and extending through the substance impervious material and through the lumen of the needle toward the end opposite the tapered end.

13. A *device* [hollow needle] as in claim 12 wherein said transducer is fixed within the needle lumen by a substance impervious adhesive and said conductors are encapsulated in and bonded to the wall of the needle by a substance impervious adhesive, and wherein the substance impervious material and substance impervious adhesive are formed to present a surface area which is substantially coincident with the opening at the tapered end of the needle.

14. A *device* [hollow needle] as in claim 12 wherein said needle includes an opening in the side thereof, and wherein said transducer unit further comprises
    an electrical insulative tube disposed in the needle lumen with one end of the tube fixed in the side opening of the needle to enable the tube interior to communicate through the opening and the other end extending toward the end of the needle opposite the tapered end.

15. A *device* [hollow unit] as in claim 14 further comprising means for supplying an electrolytic solution to said insulative tube.

16. *A chemical sensitive device for detecting chemical properties of substances to which the device is exposed comprising*
    [A] *a* split-lumen catheter having a center wall extending substantially the length of the catheter to define two lumens, [comprising the]
    *a* transducer unit [of claim 11] *including*
        *a semi-conductor substrate having a doping polarity,*
        *a pair of spaced apart diffusion regions located at the surface of said substrate material,*
        *an electrical insulator material overlying at least a portion of said diffusion regions and the surface of the substrate material lying between the diffusion regions,*
        *a chemical selective system adapted to interact with said substances and containing a chemical selective membrane overlying said insulator material,*
        *a reference electrode connected in circuit relationship with said spaced apart diffusion regions through a potential source such that a potential is created and added to the potential generated in the chemical selective membrane the combination of which affects the conductivity between said diffusion regions as a measure of the chemical properties of said substances, and*
        *a substance impervious material disposed about said substrate material, diffusion regions, insulator material and membrane and including an opening for exposing a portion of said selective system,*
    said transducer *unit* being fixed in one of the lumens near one end of the catheter so that the portion of the selective system exposed through the opening in the substance impervious material is exposed to fluid entering the other lumen, and
    electrical conductors coupled to said diffusion regions and said substrate material and extending through the substance impervious material and through one lumen toward the other end of the catheter.

17. A *device* [catheter] as in claim 16 wherein said transducer is fixed within said one lumen by a substance impervious adhesive so that the transducer and substance impervious adhesive seal said one lumen from the other lumen.

18. A *device* [catheter] as in claim 16 wherein said catheter includes an opening in the exterior wall surrounding said one lumen, and wherein said transducer unit further comprises
    an electrical insulative tube disposed in said one lumen with one end of the tube fixed in the exterior wall opening to enable the tube interior to communicate through the opening and the other end of the tube extending toward said other end of the catheter.

19. A *device* [catheter] as in claim 18 further comprising means for supplying an electrolytic solution to said insulative tube.

20. *A chemical sensitive device for detecting chemical properties of substances to which the device is exposed comprising*
    [A transducer unit as in claim 11 further comprising] a tube for carrying fluids, said tube having an opening in a side wall thereof,
    *a transducer unit including*
        *a semi-conductor substrate having a doping polarity,*
        *a pair of spaced apart diffusion regions located at the surface of said substrate material,*
        *an electrical insulator material overlying at least a portion of said diffusion regions and the surface of the substrate material lying between the diffusion regions,*
        *a chemical selective system adapted to interact with said substances and containing a chemical selective membrane overlying said insulator material, and containing an ion-exchanger which selectively reacts with certain ions when exposed to substances containing such ions to enable an exchange of ions between the ion-exchanger and the substances*
        *a reference electrode connected in circuit relationship with said spaced apart diffusion regions through a potential source such that a potential is created and added to the potential generated in the chemical selective membrane the combination of which affects the conductivity between said diffusion regions as a measure of the chemical properties of said substances, and*
        *a substance impervious material disposed about said substrate material, diffusion regions, insulator material and membrane and including an opening for exposing a portion of said selective system, and*
    said transducer *unit* being mounted on the outside of *the tube* over the opening so that the portion of the selective system exposed through the opening in the substance impervious material is also exposed through the opening in the tube to fluids passing through the tube.

21. A chemical sensitive field-effect transistor transducer for detecting different chemical properties of a substance comprising:
    a semi-conductor substrate material having a doping polarity,
    a plurality of pairs of spaced apart diffusion regions located at the surface of said substrate and having a doping polarity opposite that of the substrate material,
    electrical insulator material overlying at least portions of each diffusion region and the surface of the substrate material lying between each pair of diffusion regions,
    a plurality of chemical selective systems, each [containing] *including* a chemical selective membrane overlying the insulator material covering a different pair of diffusion regions and the substrate surface lying therebetween, *and each containing an ion-exchanger which enables a selective ion exchange between the ion-exchanger and substances containing a certain type of ion,* and a reference electrode connected in circuit relationship with each pair of spaced apart diffusion regions through a potential source such that a potential is created and added to the potential generated in each chemical selective membrane the combination of which affects the conductivity between each pair of diffusion regions as a measure of the chemical property of said substance being detected at each pair of diffusion regions.

* * * * *